(12) United States Patent
Cappel

(10) Patent No.: US 8,009,289 B2
(45) Date of Patent: Aug. 30, 2011

(54) SPECTROSCOPIC ANALYSIS METHODS

(75) Inventor: Ute Cappel, Dusseldorf (DE)

(73) Assignee: Renishaw PLC, Wotton-Under-Edge (GB)

( * ) Notice: Subject to any disclaimer, the term of this patent is extended or adjusted under 35 U.S.C. 154(b) by 330 days.

(21) Appl. No.: 12/308,258

(22) PCT Filed: Jun. 18, 2007

(86) PCT No.: PCT/GB2007/002276
§ 371 (c)(1),
(2), (4) Date: Dec. 11, 2008

(87) PCT Pub. No.: WO2007/144664
PCT Pub. Date: Dec. 21, 2007

(65) Prior Publication Data
US 2010/0027003 A1 Feb. 4, 2010

(30) Foreign Application Priority Data
Jun. 16, 2006 (GB) .................................. 0611981.2

(51) Int. Cl.
*G01J 3/40* (2006.01)
(52) U.S. Cl. ........................................ 356/301; 702/194
(58) Field of Classification Search .................. 356/303, 356/301; 702/27, 28, 194
See application file for complete search history.

(56) References Cited

U.S. PATENT DOCUMENTS 5,442,438 A 8/1995 Batchelder et al.
5,510,894 A 4/1996 Batchelder et al.

OTHER PUBLICATIONS

Young Mee Jung et al., Application of Two-Dimensional Correlation Spectroscopy to Chemometrics: Self-Modeling Curve Resolution Analysis of Spectral Data Sets, Applied Spectroscopy, vol. 57, No. 11, 2003.*
Andrew et al., "Rapid Analysis of Raman Image Data Using Two-Way Multivariate Curve Resolution," Applied Spectroscopy, 1998, vol. 56, No. 6, pp. 797-807.
Sanchez et al., "Othogonal Projection Approach Applied to Peak Purity Assessment," Anal. Chem., 1996, vol. 68, No. 1, pp. 79-85.
Windig et al., "Self-modeling mixture analysis of categorized pyrolysis mass spectral data with the SIMPLISMA approach," Chemometrics and Intelligent Laboratory Systems, 1992, vol. 14, pp. 195-207.
Brereton et al., Chemometrics-Data Analysis for the Laboratory and Chemical Plant, 2003. pp. 191-223.

(Continued)

*Primary Examiner* — Layla Lauchman
(74) *Attorney, Agent, or Firm* — Oliff & Berridge, PLC

(57) ABSTRACT

A spectroscopic analysis method in which spectral data of mixtures obtained from a plurality of points on a sample surface are resolved into component spectra and concentrations. A new alternating least squares multivariate curve resolution technique is presented which iteratively resolves the components. The technique starts from an initial estimate that the spectral values of a first component of the sample are all equal (an 'empty model'), and resolves that component. Then successive further components are iteratively resolved, from initial 'empty model' estimates of those components and from previously resolved spectra. In the common case where the main component is present in nearly pure form in the data set, this empty modelling technique results in more accurate resolution of the components. This is due to the ability of the technique to resolve the pure spectra of minor components without modelling concentrations of the main component into them.

16 Claims, 9 Drawing Sheets

OTHER PUBLICATIONS

Lawson et al., "Solving Least Squares Problems," 1974, Chapter 23, pp. 159-165.

Bro et al., "A Fast Non-Negativity-Constrained Least Squares Algorithm," *Journal of Chemometrics*, 1997, vol. 11, pp. 393-401.

Jiang et al., "On simplex-based method for self-modeling curve resolution of two-way data," *Chemometrics and Intelligent Laboratory Systems*, 2003, vol. 65, No. 1, pp. 51-65.

Edelenyi et al., "Application of independent component analysis to $^1$H MR spectroscopic imaging exams of brain tumours," *Analytica Chimica Acta*, 2005, vol. 544, No. 1-2, pp. 36-46.

Juan et al., "Spectroscopic imaging and chemometrics: a powerful combination for global and local sample analysis," *Trends in Analytical Chemistry*, 2004, vol. 23, No. 1, pp. 70-79.

Jiang et al., "Principles and methodologies in self-modeling curve resolution," *Chemometrics and Intelligent Laboratory Systems*, 2004, vol. 71, No. 1, pp. 1-12.

Gallagher et al., "Estimation of trace vapor concentration-pathlength in plumes for remote sensing applications from hyperspectral images," Proceedings of SPIE, 2003, vol. 5093, pp. 184-194.

Malinowski, "Factor Analysis in Chemistry," 2002, Section 3.3.8 NIPALS, pp. 52-54.

* cited by examiner

SPECTROSCOPIC ANALYSIS METHODS

FIELD OF THE INVENTION

This invention relates to spectroscopic apparatus and methods. It is particularly useful in Raman spectroscopy, though it can also be used in other forms of spectroscopy, e.g. using narrow-line photoluminescence, fluorescence, cathodo-luminescence or infra-red.

DESCRIPTION OF PRIOR ART

The Raman effect is a phenomenon in which a sample scatters incident light of a given frequency, into a frequency spectrum which has lines caused by interaction of the incident light with the molecules making up the sample. Different chemical compounds have different characteristic Raman spectra, and so the effect can be used to analyse the chemical compounds present.

Examples of Raman spectroscopy apparatus are known from U.S. Pat. Nos. 5,442,438 and 5,510,894, which are incorporated herein by reference. A sample is irradiated with monochromatic light from a laser. Typically the scattered light is then dispersed into a Raman spectrum by a dispersive device such as a diffraction grating, e.g. in a monochromator. The dispersed spectrum is detected by a detector such as a charge-coupled device (CCD). The resulting data may then be read into a computer for analysis.

Where a two-dimensional area of the sample is to be analysed, spectral data can be obtained for a plurality of points distributed over the area. By analysing the spectral data, images can then be produced by the computer, representing a map of the distribution of different compounds over the area of the sample. The following discussion relates to analysis of pharmaceutical samples, but it will be understood that it is equally applicable to many other types of sample.

Hyperspectral imaging data, such as can be obtained from Raman mapping experiments, can be used to obtain distribution images for different compounds present in pharmaceutical samples. Creating these images can be a complex task. In univariate methods, frequencies are selected with intensities assumed to be resulting from one compound, and images are created from the intensity variations at those frequencies. These methods require knowledge of the compounds present in the sample and their pure spectra, and problems occur if the spectra overlap and no intensities at a frequency can be clearly assigned to one spectrum. The latter problem can be overcome using the multivariate direct classical least squares method (DCLS). Here, reference spectra are used to create distribution images. However, if incomplete or no knowledge of the compounds present is available, this technique cannot be used successfully. A technique that can determine which compounds are present in the hyperspectral data is required, so that distribution images can be created.

Multivariate curve resolution (MCR) techniques can resolve the pure spectra and corresponding concentrations from mixtures and have been applied to hyperspectral data to create distribution images. One such method is the alternating least squares optimisation (ALS), which was developed for evolving data such as is obtained from chromatography experiments. Initial estimates of either the pure spectra or the concentrations are obtained and are iteratively optimised by re-calculation under constraints such as non-negativity.

A variety of methods have been used to determine the initial estimates. Some of these were developed to use evolving properties of a data set (e.g. evolving factor analysis (EFA), fixed size moving window—evolving factor analysis (FSW-EFA), and window factor analysis) but these are not well suited for image analysis. For image analysis, initial estimates can be determined from principal component analysis (PCA) or PCA followed by a Varimax rotation. Methods such as the orthogonal projection approach (OPA) and the simple-to-use interactive self-modelling mixture analysis (SIMPLISMA) determine the purest spectra or frequencies from the data set and their results can then be used to initiate the ALS optimisation. Using spectral estimates from the data set as input for the ALS algorithm works well provided the component spectra are present in near pure form in the data set. Alternatively, the intensity values at a frequency provide a good estimate for the concentrations of a component if they can be clearly assigned to a Raman band of the component spectrum.

Raman mapping data sets are often very complex, and the above conditions often only hold true for a few main components. Minor components can have very low signal levels and only occur in small proportions in any of the spectra. When using spectral estimates as input to the ALS algorithm, the algorithm often fails to improve these spectra and the resolved spectra still contain features from other component spectra. For complex many component systems, Raman bands from different compounds often overlap significantly. The overlap between bands leads to over-modelling of spectra when the ALS algorithm is initiated by concentration estimates, i.e. the resolved spectra show a dip where another resolved spectrum has a peak and the resolution of the corresponding concentration images is degraded.

Another problem for conventional MCR algorithms can be caused by the small changes that occur in Raman spectra due to crystal orientation, sample heating, or instrument perturbations. For complete analysis and resolution of all chemical components, these must be included in the analysis, but they should not disturb the resolution of the main components. If all components are modelled simultaneously, they are given equal weighting; thus signal from the main components tends to be modelled into the minor components. In such cases the model is unstable towards the main components and becomes difficult to interpret.

SUMMARY OF THE INVENTION

One aspect of the present invention provides a method for determining the components present in a sample, comprising the steps of:
  taking spectral data obtained from a plurality of points on the sample;
  making an initial estimate of spectral values of a first component of the sample;
  from the estimate of the first component, performing an iterative resolution of the spectrum of the first component; and
  making an initial estimate of spectral values of at least one further component of the sample, and performing an iterative resolution of the spectrum of each such component from the respective initial estimate and from one or more of the previously resolved spectra.

A second aspect of the invention provides a spectroscopic method for determining the components present in a sample, comprising the steps of:
  illuminating the sample;
  obtaining spectral data from a plurality of points on the sample;
  making an initial estimate of spectral values of a first component of the sample;

from the estimate of the first component, performing an iterative resolution of the spectrum of the first component; and making an initial estimate of spectral values of at least one further component of the sample, and performing an iterative resolution of the spectrum of each such component from the respective initial estimate and from one or more of the previously resolved spectra.

Preferably equal values are used for all spectral values of the respective initial estimates. Preferably the iterative resolution steps use an alternating least squares technique.

The components may be analysed as above to produce a map representing the concentrations of the components of the sample over an area thereof.

Another aspect of the invention provides spectroscopy apparatus arranged to perform the above method. The apparatus suitably includes a computer programmed to perform the steps of iteratively resolving the spectra of the components from the initial estimates.

Further aspects of the invention provide computer program code comprising instructions which, when executed by a computer, perform those steps; and a computer readable medium bearing such code:

In the method of the invention, the iteratively resolved spectral values of the components may be suitably stored as they are resolved, suitably in the computer performing the iterative resolution steps.

BRIEF DESCRIPTION OF THE DRAWINGS

Preferred methods, apparatus and examples according to the invention will now be described with reference to the accompanying drawings, wherein.

DESCRIPTION OF PREFERRED EMBODIMENTS

The preferred analytical technique developed by the inventor is a new alternating least squares technique in which components are resolved consecutively. Since equal values are used for all variables (spectral values) of the respective initial estimates, we refer to it as 'empty modelling'. Preferred implementations of the new technique are simple to use and lead to a model which is capable of resolving the pure spectra of minor components, whilst remaining very stable towards the main components (i.e. the signal of the main components is not modelled into minor components), but also allowing iterative improvement in them. The preferred technique has been applied to simulated data (example I) as well as to Raman hyperspectral imaging data from pharmaceutical samples (examples II and III), and its performance compared to the original MCR-ALS technique when using spectral or concentration estimates obtained by OPA to initiate the technique, PCA was used in all these cases to determine the number of components to resolve, and to remove noise from the data set.

EXPERIMENTAL METHODS

The data for examples II and III below were collected using an in Via Reflex Raman microscope as supplied commercially by the present applicant/assignee Renishaw, equipped with a thermoelectrically cooled RenCan CCD detector. In both cases a 10× objective was used in conjunction with 785 nm laser excitation and a 1200 lines mm grating as the dispersion element. Example II is data from a point focus mapping experiment and example m is data from a line focus mapping experiment. Both methods are hyperspectral imaging techniques. They result in a hyperspectral image cube comprising spectral values from each of a two-dimensional array of points on the sample. For point focus mapping, one spectrum is collected at a single sample point per acquisition, and this is repeated for each point in the array. In line focus mapping, the laser line is focused on the sample and several spectra from adjacent points on the sample are obtained in a single acquisition, leading to a significant time advantage compared to point focus mapping.

Figure 10:
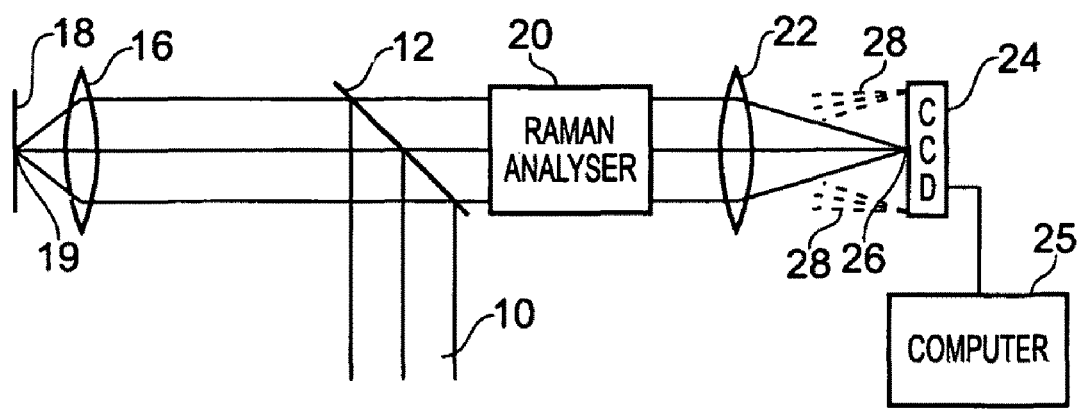
FIG. 10 is a diagrammatic representation of a Raman microscope.

The Raman microscope used is as described in the above-mentioned U.S. Pat. No. 5,442,438 and represented diagrammatically in FIG. 10 of the accompanying drawings. An input laser beam 10 is reflected through 90 degrees by a dichroic filter 12, placed at 45 degrees to the optical path. Alternatively a holographic dichroic filter may be placed at a low angle of incidence such as 10 degrees. The laser beam then passes to a microscope objective lens 16, which focuses it to a spot at its focal point 19 on a sample 18. Light is scattered by the sample at this illuminated spot, and is collected by the microscope objective lens 16 and collimated into a parallel beam which passes back to the dichroic filter 12. The filter 12 rejects Rayleigh scattered light having the same frequency as the input laser beam 10, and transmits the Raman scattered light. The Raman scattered light then passes to a Raman analyser 20.

The Raman analyser 20 comprises a dispersive element such as a diffraction grating. The light from the analyser 20 is focused by a lens 22 onto a suitable photo-detector. A two-dimensional photo-detector array is preferred. In the present embodiment the RenCam detector 24 is a charge-coupled device (CCD), which consists of a two-dimensional array of pixels, and which is connected to a computer 25 which acquires data from each of the pixels and analyses it as required. The analyser 20 produces a spectrum having various bands as indicated by broken lines 28, spread out in a line along the CCD 24.

The sample 18 may be mounted on an X-Y table so that the focal point 19 can be scanned across it in X and Y directions, e.g. under control of the computer. One spectrum is then collected at each sample point per acquisition (Example II). This enables mapping of an area of the sample. The focal point 19 may also be adjustable in the depth direction, either by movement of the sample 18 or of the lens 16 along the optical axis. Again, this may be under the control of the computer 25.

Since the detector 24 is two-dimensional, it is also possible to obtain spectra from multiple points on the sample simultaneously, by focusing the laser in a line on the sample, orthogonal to the direction of dispersion of the spectra (Example III). Several spectra from adjacent points along the line are read off the non-spectral CCD dimension in a single acquisition, leading to a significant time advantage compared to point focus mapping.

The computer 25 may also be programmed with software code on a suitable medium, comprising instructions to perform the analysis routines described in this specification. Alternatively, as described below, the spectral data obtained may be transferred to a separate computer having such software for this analysis. In either case, as the analysis proceeds, the resolved spectral values of the components are stored in the computer concerned, and may be further processed and output or displayed as maps showing the concentrations of the components in the sample.

Example I

Simulated Mixture Spectra

Figure 2:
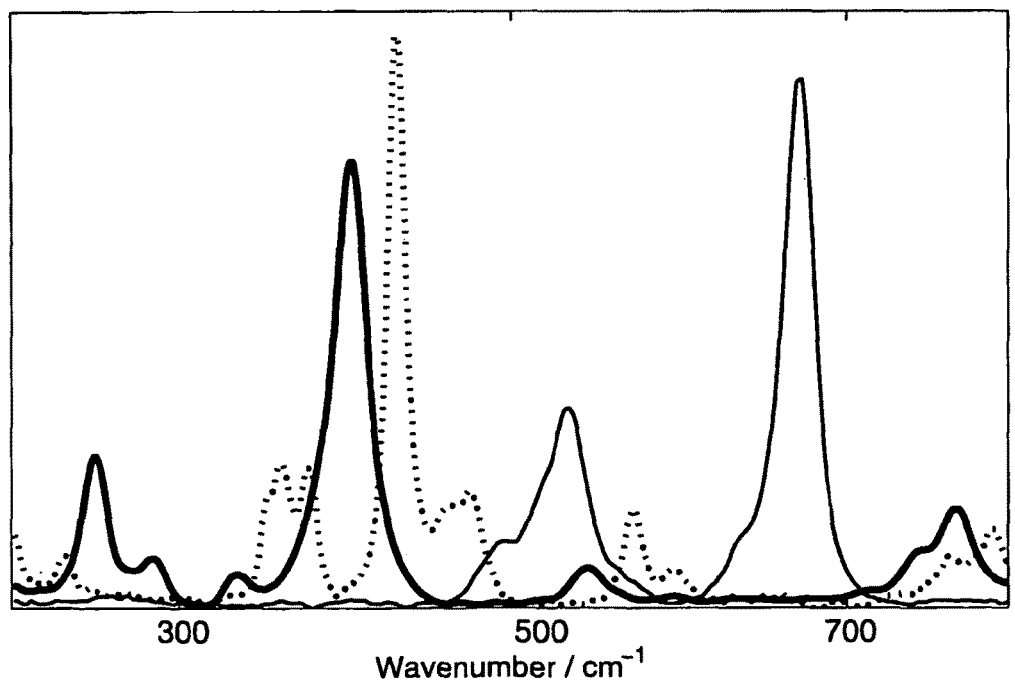
FIG. 2 shows spectra used to simulate the mixture data set for example I: component 1 spectrum (thick line), component 2 spectrum (thin line), component 3 spectrum (dashed line).

The pure Raman spectra of three pigments (FIG. 2) were added in different proportions to create a matrix of 2500 mixed spectra. The average, minimum and maximum proportions for each pigment spectrum are given in Table I. Spectra 1 and 2 were present throughout the data set whilst spectrum 3 was only present in 100 of the spectra to simulate a minor component. Random noise with Poissonian statistics was added to the data set to simulate the perturbations occurring from noise. The spectra used to create the data set were normalized by minimum value subtraction and division by the sum of their intensities. This removes intensity ambiguities from the data set and facilitates a direct comparison of ALS methods.

Example II

Pharmaceutical Powder

The analysed sample was a powdered mixture, which comprised 1% of an active pharmaceutical ingredient (API) and 99% excipients, including cellulose, lactose and dicalcium phosphate. The sample surface was flattened and a point focus map was collected from the surface. The map area was 600 µm×66 µm with a step size of 6 µm, giving 1,212 collected spectra.

Example III

Ranitidine Tablet

A commercially available tablet containing 75 mg of ranitidine as the API was analysed. The API made up approximately 50% of the total tablet mass. The excipients present in the core were microcrystalline cellulose and magnesium stearate. The tablet was cut horizontally using a scalpel. A line focus map was collected from an area of 1.68 mm×1.95 mm. With a step size of 6 µm in x and an inherent step size of 5.81 µm in y, this gave 94,000 collected spectra.

Theory

Figure 1:
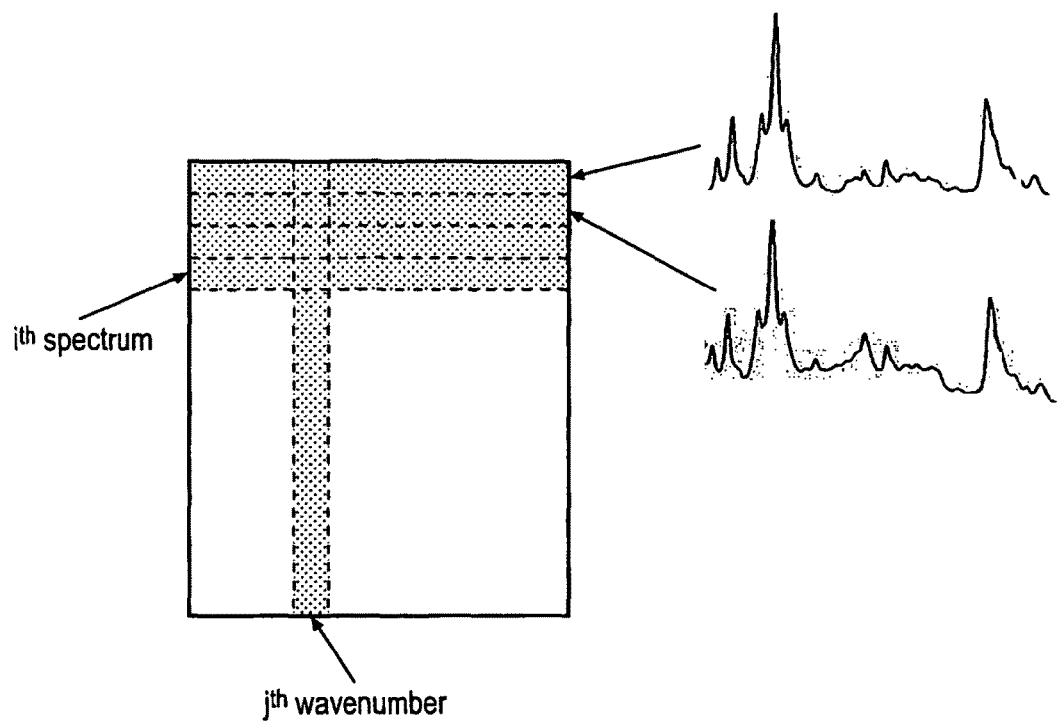
FIG. 1 shows the arrangement of hyperspectral data in a matrix.

For chemometric analysis, the hyperspectral image cube is unfolded into a matrix X, so that each collected spectrum occupies a row of the data matrix (FIG. 1). The matrix has dimensions I×J where I is the total number of spectra from the data set and J is the number of variables, which are the frequencies at which the intensities were collected. The aim of curve resolution is to decompose this matrix into the physically meaningful submatrices C and S:

$$X = C \cdot S^T + E \quad (1)$$

For a data set modelled by n components, C is an I×n matrix, where each column corresponds to the concentration values of a component, and S is a J×n matrix, where each column represents a component spectrum. E is the residual matrix with the same dimensions as X. Curve resolution techniques seek to minimise the values in this matrix.

Determination of Number of Components

In principal component analysis, the matrix X is decomposed into scores and loadings, which represent the principal components (PCs):

$$X = T \cdot V + E \quad (2)$$

The scores T and the loadings V are linear combinations of C and $S^T$ but they are not physically meaningful solutions of Eq. 1, i.e. the principal components do not represent the chemical components. The principal components are orthogonal to each other and calculated so that each component explains as much of the data variance as possible. Therefore, in a case where the data is well modelled by n components, the first n principal components will represent the signal and later components merely show noise.

The number n can be determined from the variance that each component explains: once the components show only noise the data variance explained by each component drops to a fairly constant value. For Raman data however, we have found it more reliable to use auto-correlation values of the loadings to determine whether components show spectral features or noise. This is possible since the data sets are oversampled in frequency, and thus signal levels at adjacent frequencies in a spectrum are correlated.

The point-to-point correlations of the loadings vectors are calculated as $$AUTO_k = \sum_{j=1}^{J-1} v_{kj} v_{k(j+1)} \quad (3)$$

where $v_k$ is the loadings vector of the kth PC. For values close to one, the points are highly correlated and the principal component represents signal. For values around zero, the correlation is low and the principal component represents noise. The plot of auto-correlation values against number of PC shows a sharp drop-off at n. All principal components after n can be discarded and X can be recalculated from the first n PCs to produce a noise-filtered data set.

Selection of Initial Estimates

The orthogonal projection approach can be used to obtain initial estimates for spectra as well as concentrations. The purest spectra and frequencies (variables) in the data set are determined by finding those that are most dissimilar. The dissimilarity coefficient between two row vectors placed in a matrix $Y_i$ is given by:

$$k_i = det(Y_i \cdot Y_i^T) \qquad (4)$$

When OPA is used to find the purest spectra, $Y_i$ is a Matrix containing the mean spectrum from X and the ith sample spectrum:

$$Y_i = \begin{bmatrix} x_m \\ x_i \end{bmatrix} = \begin{bmatrix} \text{average spectrum} \\ \text{ith spectrum} \end{bmatrix}$$

The dissimilarity coefficient is calculated for each spectrum in the data set and the spectrum with the highest value for k is identified as the first component spectrum.

The mean spectrum is then replaced by this spectrum in:

$$Y_i = \begin{bmatrix} \text{1st component spectrum} \\ \text{ith spectrum} \end{bmatrix}$$

The coefficients are recalculated according to Eq. 4 to determine the next most pure spectrum and the matrix is extended to include this second component spectrum. This procedure is repeated until the required number of purest spectra have been found.

To find pure frequencies rather than pure spectra, the same method can be used. The dissimilarity coefficients are then calculated for the columns of X (frequencies) rather than for the rows (spectra).

MCR-ALS

In the alternating least squares optimisation, an estimate of either S or C is used to solve Eq. 1 for the other unknown, with the solution constrained to ensure a physically meaningful result. This solution is then used to recalculate an improved value for the estimated matrix with physically meaningful constraints as before. This process is repeated until the model converges. We use the percentage lack of fit (lof) to test for convergence, which is calculated using Eq. 5.

$$lof = 100 \cdot \sqrt{\frac{\sum_{i=1}^{I} \sum_{j=1}^{J} e_{ij}^2}{\sum_{i=1}^{I} \sum_{j=1}^{J} x_{ij}^2}} \qquad (5)$$

The iteration is said to have converged, when the change in lack of fit between two consecutive iterations is smaller than a threshold value.

The constraints which can be applied depend on the type of data. Non-negativity of concentrations and/or spectra is the most common constraint and is applicable in most cases. This can be achieved by obtaining a least squares solution for Eq. 1, which minimises E, and by setting all negative values in the solution to zero. Equation 1 may also be solved using a non-negative least squares algorithm, such as non-negativity-constrained linear least squares (NNLS) or fast non-negativity-constrained least squares (FNNLS). These algorithms provide a superior solution as they ensure that a least squares solution is obtained under non-negativity constraints. In addition, the concentrations can be constrained to additivity to one, so that for a sample point the sum of all concentration values is one. Unimodality (i.e. one local maximum in the concentrations of a component) and selectivity (e.g. zero-concentration windows) constraints have also been used for chromatography data but these are usually not applicable to spectroscopic imaging data.

Empty Modelling

For the empty modelling algorithm, an 'empty spectrum' is created as an estimate for the first component spectrum. This empty spectrum has all intensities equal, with value dependent on the normalisation of the spectra in X. ALS optimisation is used to model the first component spectrum. Non-negativity of C and S is enforced using the FNNLS algorithm, and the resolved spectrum is length constrained to a value in accordance with the normalisation of the data matrix. In the next iteration, the resolved spectrum plus another empty spectrum are used to reinitialise the ALS optimisation. The same constraints are applied and the concentrations are also constrained to additivity to one. After each iteration another empty spectrum is added, until all significant components have been resolved. The concentrations and spectra obtained in the last optimisation are the final solution of empty modelling.

The stepwise resolution of component spectra implies that the components are not equivalent, i.e. there are major and minor components. The first component will be modelled to the mean spectrum in the first iteration and optimised to show the spectrum of the main component later. In order for this process to produce a good representation of the main component spectrum it must be present in nearly pure form in the data set.

Analysis Methods

Chemometric analysis of the data sets from the above Examples was carried out in MATLAB R2006a (The Math-Works Inc., Natick, Mass.). Examples. I and II used an HP Compaq dc5100 computer with a 32-bit, 2.8 GHz Pentium 4 processor and 1.25 GB of physical memory running Microsoft Windows XP Professional. Example III was analysed using the 64-bit version of MATLAB R2006a on an Evesham PC with a 64-bit, 2.01 GHz AMD Athlon 64×2 dual core 3800+ processor and 512 Mb of physical memory running Microsoft Windows XP Professional x64. The increased address space available in this architecture was required to analyse the larger data set of example III.

Cosmic ray features were removed from data sets II and III using a nearest neighbour comparison method. PCA was performed on all data sets to determine the number of components and remove noise. The resulting spectra were processed by subtracting the minimum value of each spectrum and scaling to unit intensity sum. This was done to remove intensity differences for example due to laser power or focus changes. It ensures that additivity to one of the concentrations is a feasible constraint. Estimates for concentrations and pure spectra were obtained by OPA. Final component spectra and concentrations were modelled by MCR-ALS using the concentration estimates from OPA to initiate the optimisation (OPA(conc)/MCR-ALS), by MCR-ALS using the spectra from OPA (OPA(spec)/MCR-ALS) and by empty modelling. In all cases, both spectra and concentrations were constrained to non-negativity using the FNNLS algorithm. The concentrations were constrained to additivity to one and the spectra were constrained to unit intensity sum.

Where reference spectra were available, the results of the different algorithms were compared by calculating correlation coefficients (Eq. 6) between mean-centred resolved spectra ($s_k$) and mean-centred reference spectra ($s_r$).

$$\text{corr} = 1 - \frac{(s_k - s_r)^2}{(s_k \cdot s_k)(s_r \cdot s_r)} \quad (6)$$

For the simulated data of example I the actual concentration values are known and may be used to compare the different approaches. The rms deviations of the resolved concentrations from their known values were therefore calculated in this case.

Results and Discussion

Example I

Simulated Mixture Spectra

Figure 3:
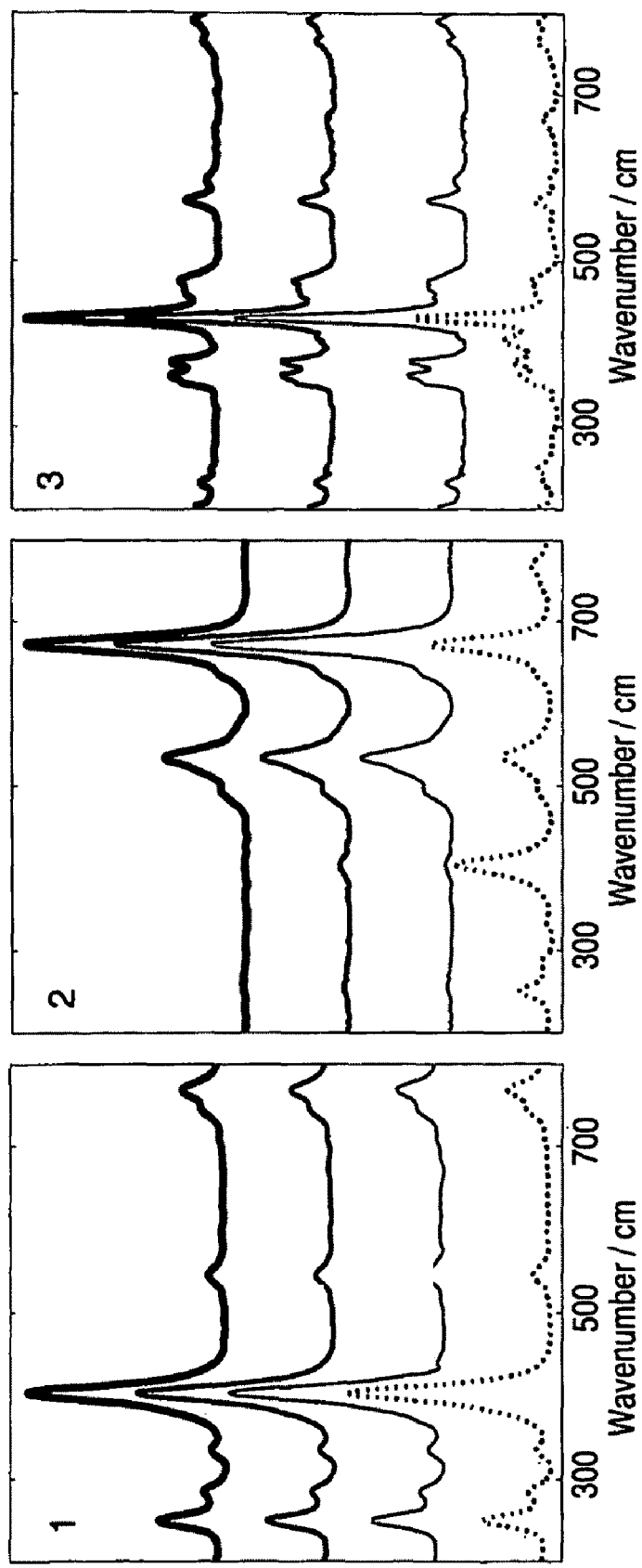
FIG. 3 shows component spectra from the simulated mixture of example I for components 1, 2 and 3: reference spectra (thick line), spectra resolved by empty modelling (medium line), spectra resolved by OPA(conc)/MCR-ALS (thin line), spectra resolved by OPA(spec) MCR-ALS (dashed line).

PCA shows clearly that there are 3 components in the data set, as expected. The reference spectra and the component spectra that were resolved by the different MCR methods are shown in FIG. 3. A numerical comparison of the models is given in Table I. The component 1 spectrum resolved by OPA(spec)/MCR-ALS matches the reference spectrum well, but the other two component spectra also show features of the first. Concomitant with this is a shift in concentration from component 1 to the latter two, resulting in poor predictions of the concentration values.

With OPA(conc)/MCR-ALS all spectra appear to be reasonably well resolved, although the correlation of component 1 spectrum with the reference spectrum is an order of a magnitude worse than the resolution of this spectrum by the other two methods. The poorer resolution of this spectrum is most apparent in a slight dip on the high wavenumber edge of its main Raman band at 400 cm$^{-1}$. On this edge, the band overlaps with the strongest band in the component 3 spectrum, and therefore the component 1 spectrum is over-modelled. This strongly reflects in the concentration values. The range of concentration values for the first component is too narrow and its average concentration too low. In the case of component 3, the rms deviation of the concentrations from the known values is very high compared to the average proportion. The minimum concentration value for this component is 2.13%, even though this component is only present in 100 of the 2500 spectra, and the average concentration is too high by a factor of six. So, in spite of good spectral correlation values, the concentrations of component 1 and 3 are not well resolved and concentration images would not reflect the actual distribution. On the other hand, for component 2, where the main Raman bands are well separated from the Raman bands of the other component spectra, both the spectrum and concentrations correspond well to the reference spectrum and the actual values.

With empty modelling all component spectra are well resolved, in particular the spectrum of the first component. This also leads to low rms deviations of the resolved concentrations from their known values. Apart from the case of component 2 resolved by OPA(conc)/MCR-ALS, all rms concentration deviations are better for the empty modelling results than for those of the other techniques. The resulting concentrations are therefore a more accurate reflection of the real values.

Example II

Pharmaceutical Powder

Figure 4:
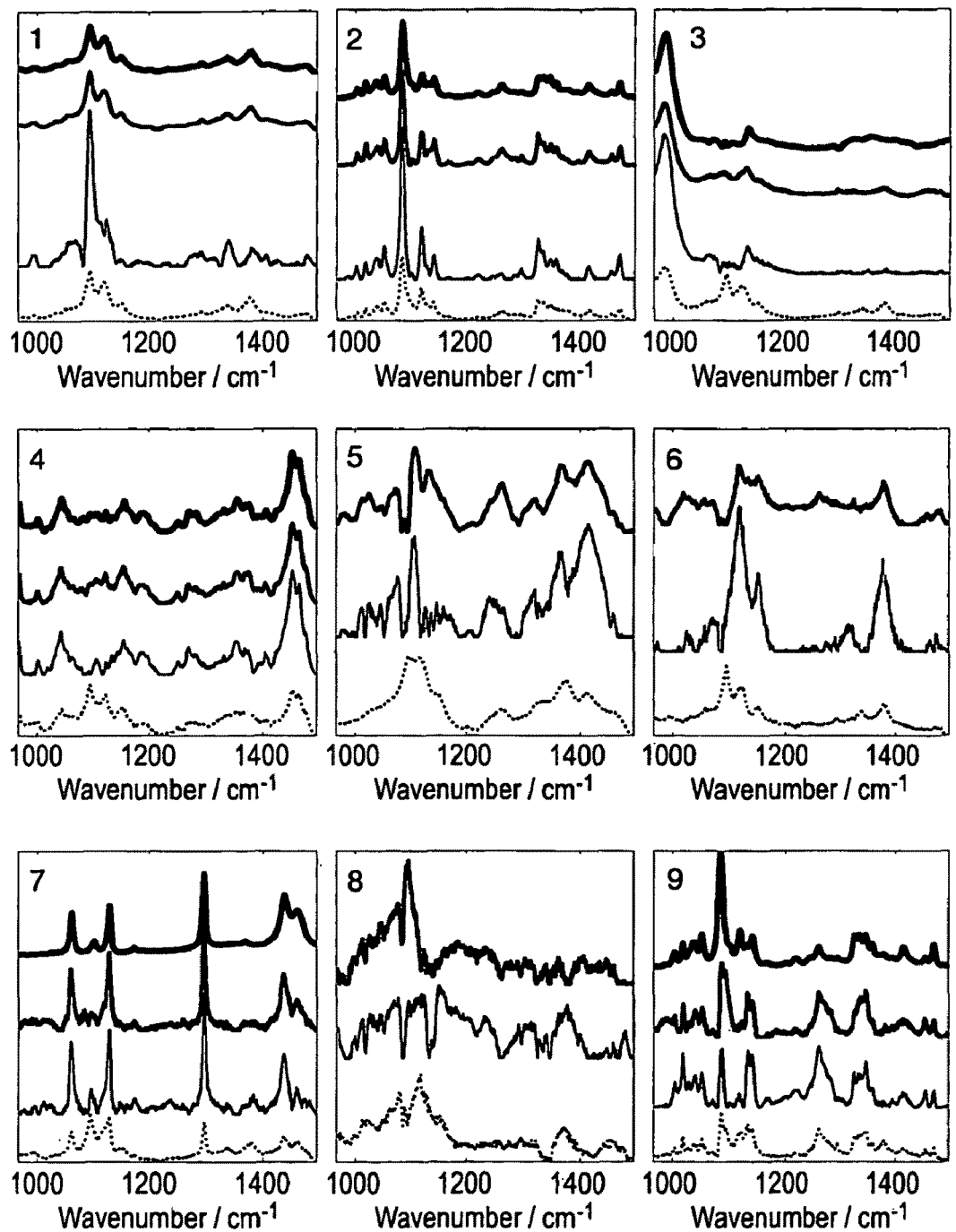
FIG. 4 shows spectra from powder sample of example II: reference spectra (where available) (thick line), spectra resolved by empty modelling (medium line), spectra resolved by OPA(conc)/MCR-ALS (thin line), spectra resolved by OPA(spec) MCR-ALS (dashed line). Lactose reference spectrum is shown for component 2 and 9.
Figure 5:
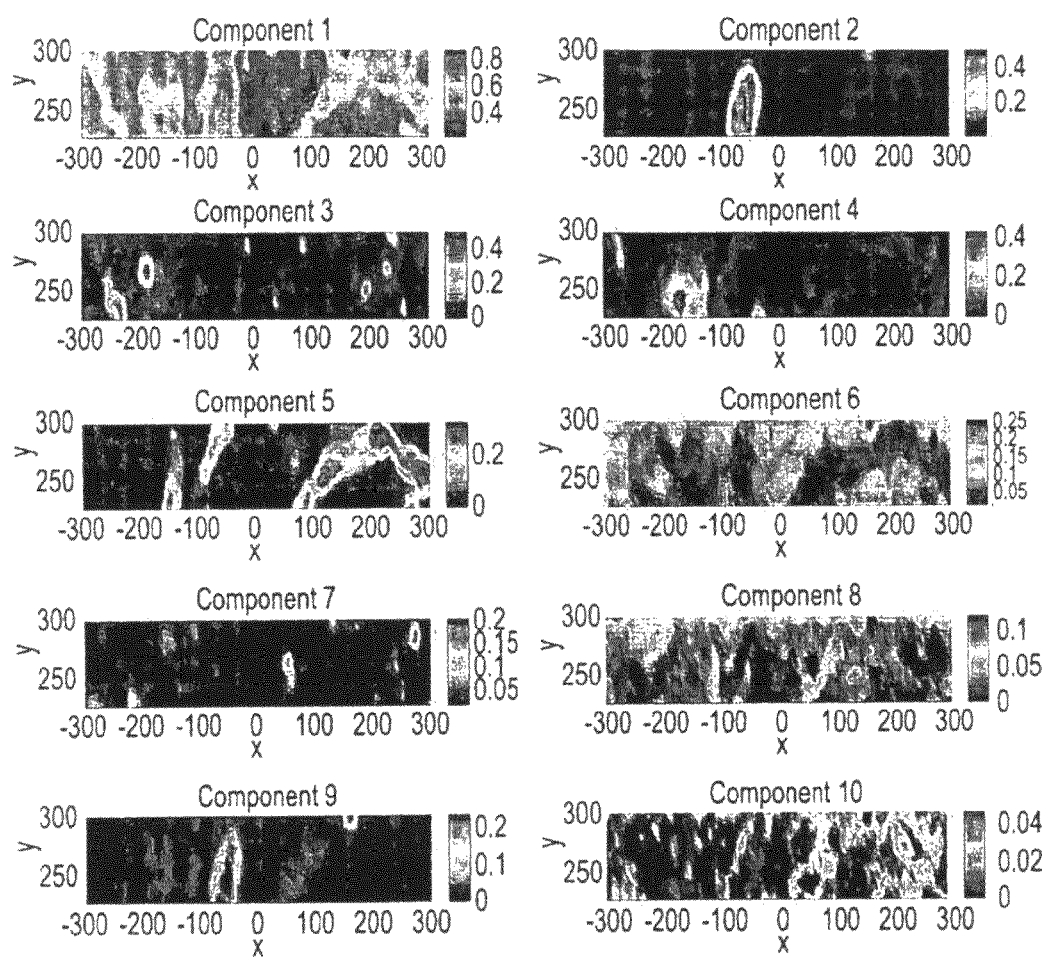
FIG. 5 shows concentration images from example II, obtained using an "empty modelling" technique in accordance with the present invention.

Principal component analysis of the map data showed that ten components are present in the data set. The ten components were resolved by the three MCR-ALS techniques as described previously. Results of the different methods are shown in Table II. The first nine resolved spectra, compared to reference spectra where available, are given in FIG. 4 and the images from empty modelling are given in FIG. 5.

The empty modelling results can be interpreted as follows. There are six components that represent independent compounds: cellulose (component 1), lactose (component 2), dicalcium phosphate (component 3), the API (component 4), an unidentified excipient (component 5) and magnesium stearate (component 7). Components 6, 8 and 10 result from baseline variations. Component 9 is due to different rotational variations between the two lactose crystals (compare the images of component 2 and 9 in FIG. 5).

These observations are less obvious from the OPA(spec)/MCR-ALS results. Cellulose and lactose are very well resolved (even better than by empty modelling due to an overlap between peaks in the two spectra), but the resolution of the minor components is poor. The resolved spectra of dicalcium phosphate, the API and magnesium stearate all contain features from the cellulose spectrum, as do the components that depict baseline changes in the empty modelling analysis. This poor resolution leads to a shift in average concentration values compared to those obtained from empty modelling. The first component has a much lower concentration in the OPA(spec)/MCR-ALS model, while the other average concentration values are higher than the empty modelling ones.

Dicalcium phosphate and the API are well resolved by OPA(conc)/MCR-ALS, but the signal from cellulose becomes modelled into at least two components (1 and 6), and the match with the cellulose reference spectrum is poor. With a 10 component model, the results from OPA(conc)/MCR-ALS can be used to prove the presence of lactose, dicalcium phosphate and the API, but the corresponding concentration images are low in contrast and difficult to interpret. The concentration values suggest that at least 8 components are present in each map point, while the empty modelling results suggest the main component (cellulose) is present everywhere, with the minor components present only in localised particles (see Table II and FIG. 5). The good resolution of the cellulose spectrum by empty modelling suggests that this is true, and that the concentrations from OPA(conc) MCR-ALS are likely to be inaccurate (as in example I).

Figure 6:
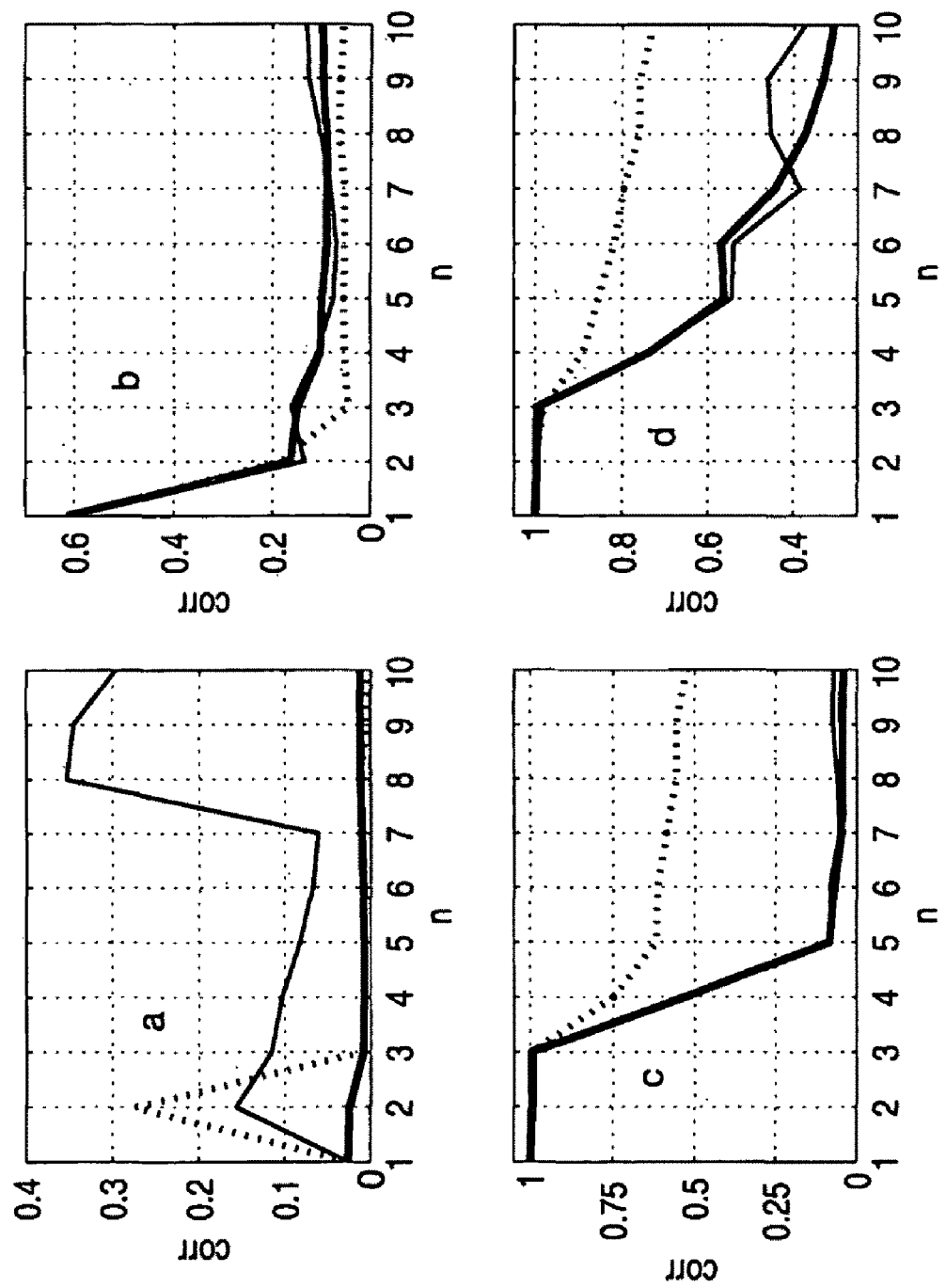
FIG. 6 shows spectral correlation values for different numbers of resolved components in example II, (a) cellulose (component 1), (b) lactose (component 2), (c) API (component 4), (d) magnesium stearate (component 7). Values from empty modelling (thick line), values from OPA(conc)/MCR-ALS (thin line), values from OPA(spec)/MCR-ALS (dashed line).

The relatively large number of components present causes part of the resolution problem for MCR(conc)/MCR-ALS. No truly pure frequencies can be selected for the later components, as they are due to baseline changes, and there is a large overlap between the estimates. This causes the final concentration values of a single spectrum to be split between the components, and the real spectra to be linear combinations of the resolved component spectra. For comparison, all methods were repeated with varying numbers of components (1 to 10). The correlation values of the resolved spectra with the cellulose, the lactose, the API, and the magnesium stearate reference spectra are shown in FIG. 6. For lactose and the API, the correlation values drop once the component has been resolved, and then remain relatively constant with a slight increase towards the end for OPA(conc)/MCR-ALS. For cellulose, the values are low for OPA(spec)/MCR-ALS and empty modelling (except for the 2 component OPA(spec)/MCR-ALS model). For OPA(conc)/MCR-ALS, the correlation values decrease after 2 components until 7 components, though they are never as low as the OPA(spec)/MCR-ALS or the empty modelling ones. There is a sharp increase in correlation for the 8 component model. At this point, the cellulose signal becomes modelled into two components. For magnesium stearate, the correlation values of OPA(conc)/MCR-ALS and empty modelling show a sharp decrease when the API is resolved as there is some overlap between the API and the magnesium stearate spectrum. Another drop is observed at 7 components, when the magnesium stearate spectrum is resolved.

Figure 7:
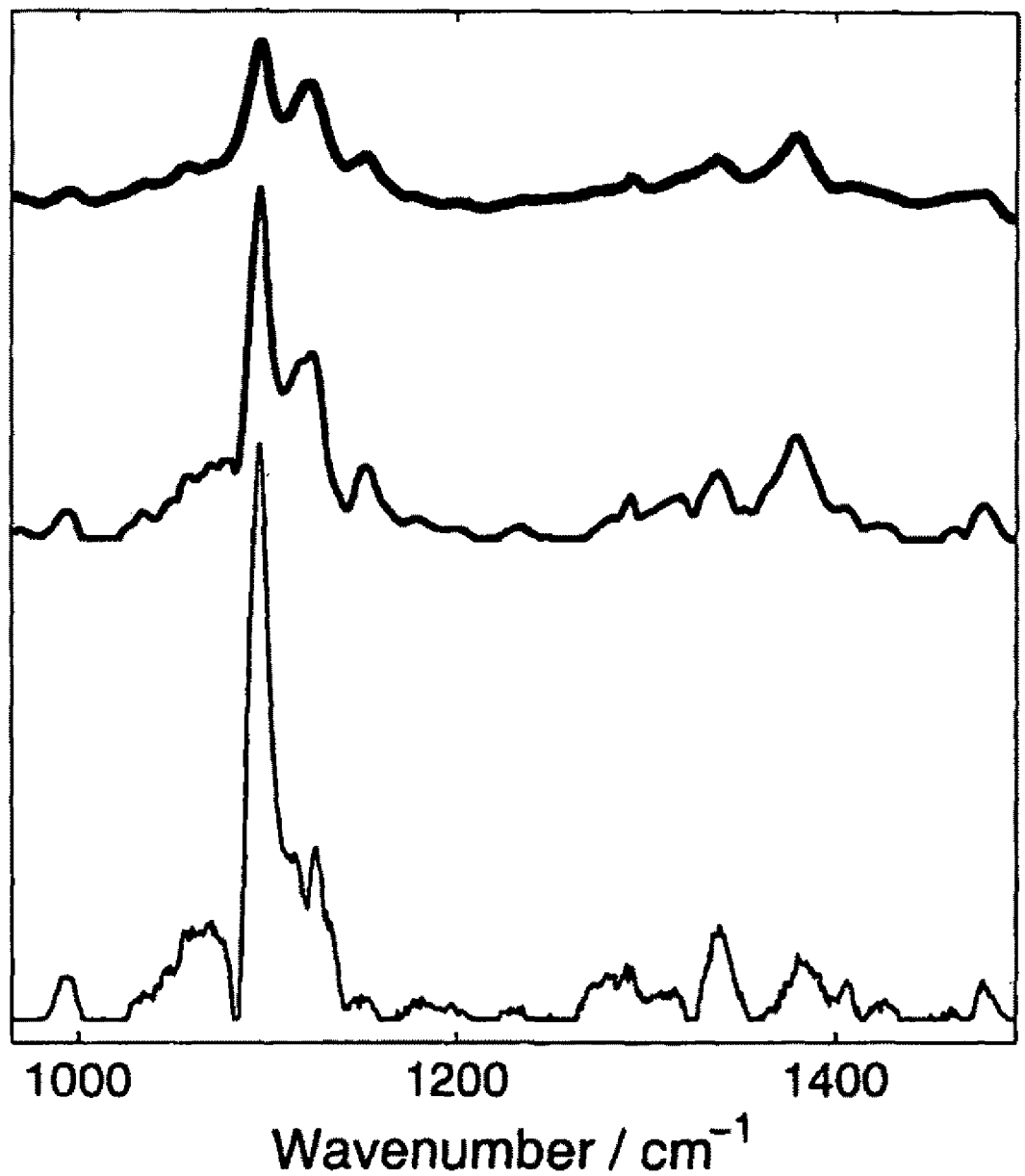
FIG. 7 shows a cellulose spectrum resolved by OPA(conc)/MCR-ALS in example II. Reference spectrum (thick line), spectrum resolved in model with 7 components (thin line), spectrum resolved in model with 10 components (medium line).

For OPA(conc)/MCR-ALS, the model in greatest correspondence with the reference spectra is obtained using 7 initial estimates. The resolution of the cellulose spectrum with a 7 component model compared to the 10 component model and the reference spectrum can be seen in FIG. 7. Even with 7 components, the resolved cellulose spectrum is still over-modelled and the concentration values are likely to be inaccurate.

For empty modelling, the 10 component model shows the greatest correspondence with the reference spectra. A good match with reference spectra is observed once a component is first resolved, and after that the improvement is only small. The model is very stable with an increasing number of components. This is a logical consequence of the iterative modelling, as resolved components are included in the modelling of the new components. In contrast to this for the OPA/MCR-ALS cases, a new model is created for each different number of components.

Example III

Ranitidine Tablet

The overall concentration of API in the tablet is over 50% by weight. As the tablet has a coating, the percentage of API will be even higher in the tablet core. APIs are also usually stronger Raman scatterers than excipients. It is therefore reasonable to assume that spectra of the API will be present in the data set in a relatively pure form and that the condition required for empty modelling should be fulfilled.

Figure 8:
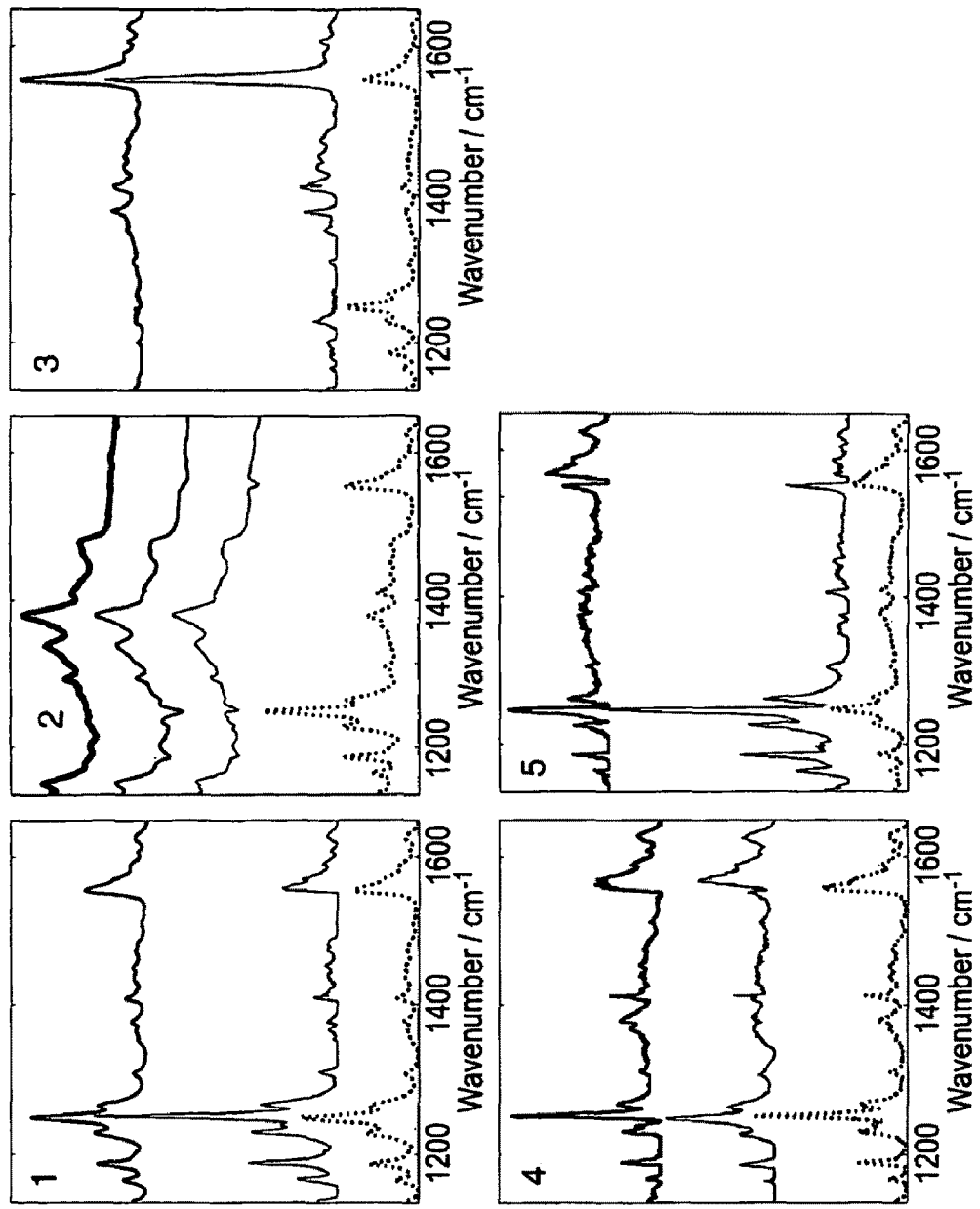
FIG. 8 shows spectra from a rantidine tablet of example III: cellulose reference spectrum (thick line), spectra resolved by empty modelling (medium line), spectra resolved by OPA (conc)/MCR-ALS (thin line), spectra resolved by OPA(spec) MCR-ALS (dashed line).
Figure 9:
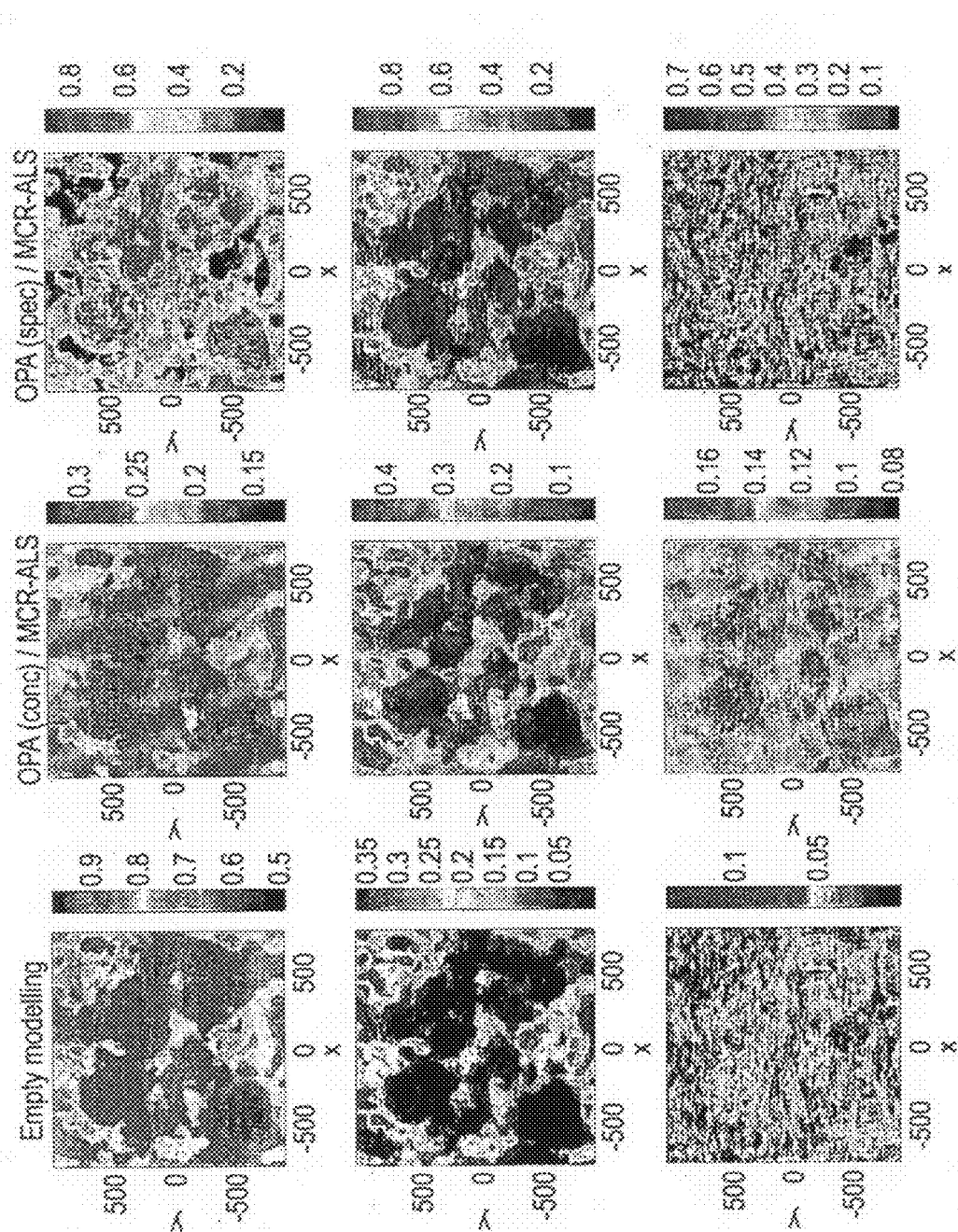
FIG. 9 shows concentration profile images from the rantidine tablet of example III, first row: component 1 (API), second row: component 2 (cellulose), third row: component 3 (intensity variations in drug peak).

PCA determined that five components are present in the data set. Spectra of the components resolved by the different MCR methods can be seen in FIG. 8 and numerical results are given in Table III. The first component corresponds to form H of ranitidine hydrochloride. The data set contains spectra that are very similar to this, and the first spectra resolved by OPA(spec)/MCR-ALS and empty modelling match it well. The second component corresponds to cellulose, for which a reference spectrum is included in FIG. 8. The component 2 spectra resolved by OPA(conc)/MCR-ALS and empty modelling match this reference spectrum well, apart from slight dips that correspond to peaks in the API spectrum. The third component represents intensity variations between the different API peaks, the fourth component a slight shift to high wavenumber in the main API bands, and the fifth a slight shift to low wavenumber. No component representing magnesium stearate was found. Images for the first three components can be seen in FIG. 9.

As seen in the other examples, OPA(spec)/MCR-ALS fails to resolve the pure spectra of minor components—cellulose in this case—and the concentration values for these components are comparatively high. Apart from the second component, the spectra resolved by OPA(conc)/MCR-ALS are versions of the API spectrum with only some or parts of the API peaks present in each. Concentrations are divided between these components and corresponding images are low in contrast.

In the empty modelling analysis, the variation in the API spectrum is modelled into the last three components resolved, though the main API component maintains a high average concentration due to the previously mentioned stability of the algorithm towards main components. The overall API distribution can be seen in its image. The later images show the locations where variations in the API spectrum occur, e.g. the component 3 image could give an indication of the particle sizes as the intensity variations between the API peaks are likely to result from crystal rotations. The results of empty modelling are therefore easiest to understand: components 1 and 2 show the chemical components and their distribution, whilst components 3 to 5 show the small changes in the spectrum of the main component, and where those changes occur on the sample surface.

CONCLUSION

Multivariate curve resolution techniques are good methods for obtaining images from Raman mapping data as they do not require any prior knowledge of the data. Using alternating least squares in combination with spectral estimates from the data set provides images in accordance with the spectra present in the data set. However, it often fails to resolve underlying pure component spectra and thus identification of minor components becomes difficult, and concentration values do not represent the proportions of the true components.

Using alternating least squares in combination with concentration estimates is a good method for resolving the spectra of minor components. However, the model can be unstable as the number of components changes and resolution of major components is heavily influenced by small spectral changes and overlapping peaks, which can lead to over-modelled spectra. In such cases the concentration values are inaccurate, and for minor chemical components they are often greater than zero in all places even though the component is only present in a small area.

For data sets where a main component is present in nearly pure form, which is a common situation, the empty modelling algorithm overcomes the drawbacks of both conventional methods by resolving and improving the component spectra iteratively. This ensures accurate resolution of the major components irrespective of the number of components modelled, whilst also correctly resolving the pure spectra of minor components. The method has great potential in identifying unknowns in a mixture and also in providing corresponding concentration images, which clearly show where each component is present. Small spectral changes can be modelled so that the method can be used to identify crystal rotations and structural changes (e.g. different polymorphic forms of a compound). In addition, the method could be automated easily as no selection of initial estimates is required, and the results obtained are easier to interpret than the conventional MCR-ALS models as components are resolved in order of their importance.

TABLE 1

Results from Example I

| Component | 1 | 2 | 3 |
|---|---|---|---|
| *Actual concentrations* | | | |
| average/% | 73.9 | 25.3 | 0.76 |
| minimum/% | 35.5 | 0.69 | 0 |
| maximum/% | 99 | 50 | 33.2 |
| *Empty modelling* | | | |
| average/% | 75.2 | 23.6 | 1.18 |
| minimum/% | 36.5 | 0 | 0 |
| maximum/% | 99.9 | 49.8 | 33 |
| spectral correlation | $3.51 \cdot 10^{-4}$ | $1.13 \cdot 10^{-3}$ | $3.51 \cdot 10^{-4}$ |
| rms deviation of conc./% | 1.36 | 1.73 | 0.526 |
| *OPA(conc)/MCR-ALS* | | | |
| average/% | 70.2 | 25.1 | 4.75 |
| minimum/% | 36.3 | 0.85 | 2.13 |
| maximum/% | 92.9 | 50.2 | 32.6 |
| spectral correlation | $4.39 \cdot 10^{-4}$ | $5.32 \cdot 10^{-4}$ | $4.07 \cdot 10^{-3}$ |
| rms deviation of conc./% | 4.04 | 0.702 | 4.13 |
| *OPA(spec)/MCR-ALS* | | | |
| average/% | 50.1 | 47.3 | 2.62 |
| minimum/% | 0 | 0 | 0 |
| maximum/% | 97.1 | 98.4 | 50.2 |
| spectral correlation | $4.47 \cdot 10^{-4}$ | $4.46 \cdot 10^{-1}$ | $1.57 \cdot 10^{-1}$ |
| rms deviation of conc./% | 27.1 | 25.9 | 2.79 |

TABLE 2

Results from Example II

| Component | 1 | 2 | 3 | 4 | 5 | 6 | 7 | 8 | 9 | 10 |
|---|---|---|---|---|---|---|---|---|---|---|
| *Empty modelling* | | | | | | | | | | |
| average/% | 65.7 | 5.03 | 4.67 | 4.46 | 5.89 | 7.04 | 1.48 | 2.89 | 1.91 | 0.97 |
| minimum/% | 21.0 | 0 | 0 | 0 | 0 | 0 | 0 | 0 | 0 | 0 |
| maximum/% | 86.0 | 50.0 | 48.7 | 43.0 | 31.8 | 25.8 | 21.1 | 11.9 | 23.6 | 4.64 |
| corr | $1.21 \cdot 10^{-2}$ | $9.90 \cdot 10^{-2}$ | $1.12 \cdot 10^{-1}$ | $4.25 \cdot 10^{-2}$ | — | — | $3.06 \cdot 10^{-1}$ | — | — | — |
| *OPA(conc)/MCR-ALS* | | | | | | | | | | |
| average/% | 20.6 | 11.6 | 6.21 | 7.64 | 11.2 | 16.4 | 3.44 | 8.55 | 7.64 | 6.67 |
| minimum/% | 10.4 | 7.88 | 1.94 | 3.04 | 4.78 | 6.89 | 0.14 | 0 | 0.93 | 0 |
| maximum/% | 29.7 | 34.4 | 34.4 | 36.1 | 25.4 | 19.8 | 19.3 | 20.4 | 33.7 | 12.3 |
| corr | $2.96 \cdot 10^{-1}$ | $1.31 \cdot 10^{-1}$ | $3.23 \cdot 10^{-2}$ | $7.28 \cdot 10^{-2}$ | — | — | $3.73 \cdot 10^{-1}$ | — | — | — |
| *OPA(spec)/MCR-ALS* | | | | | | | | | | |
| average/% | 36.0 | 5.02 | 6.46 | 5.63 | 15.3 | 7.44 | 3.88 | 5.36 | 2.91 | 12.0 |
| minimum/% | 0 | 0 | 0 | 0 | 0 | 0 | 0 | 0 | 0 | 0 |
| maximum/% | 79.1 | 85.1 | 89.9 | 81.3 | 80.9 | 48.6 | 60.5 | 22.0 | 59.2 | 57.3 |
| corr | $2.93 \cdot 10^{-3}$ | $5.51 \cdot 10^{-2}$ | $4.45 \cdot 10^{-1}$ | $5.23 \cdot 10^{-1}$ | — | — | $7.29 \cdot 10^{-1}$ | — | — | — |

TABLE 3

Results from Example III

| Component | 1 | 2 | 3 | 4 | 5 |
|---|---|---|---|---|---|
| *Empty modelling* | | | | | |
| average/% | 85.6 | 9.13 | 3.09 | 1.55 | 0.64 |
| minimum/% | 49.4 | 0 | 0 | 0 | 0 |
| maximum/% | 98.1 | 36.6 | 14 | 11.2 | 21.4 |
| corr | — | $2.94 \cdot 10^{-2}$ | — | — | — |
| *OPA(conc)/MCR-ALS* | | | | | |
| average/% | 28.1 | 18.1 | 13.9 | 21.5 | 18.5 |
| minimum/% | 12.2 | 3.77 | 7.58 | 7.59 | 7.31 |
| maximum/% | 32.8 | 45.9 | 17.8 | 49.9 | 22.9 |
| corr | — | $1.63 \cdot 10^{-2}$ | — | — | — |
| *OPA(spec)/MCR-ALS* | | | | | |
| average/% | 48.6 | 25.4 | 17.5 | 2.46 | 6.01 |
| minimum/% | 0 | 0 | 0 | 0 | 0 |
| maximum/% | 89.6 | 95.6 | 74.2 | 14.7 | 77.2 |
| corr | — | $9.22 \cdot 10^{-1}$ | — | — | — |

The invention claimed is:

1. A method for determining the components present in a sample,
in which a computer uses spectral data obtained from a plurality of points on the sample, the method comprising:
making an initial estimate of spectral values of a first component of the sample;
from the estimate of the first component, performing an iterative resolution of the spectrum of the first component;
making an initial estimate of spectral values of at least one further component of the sample; and
performing an iterative resolution of the spectrum of each such component from the respective initial estimate and from one or more of the previously resolved spectra;
wherein equal values are used for all spectral values of a respective initial estimate.

2. A spectroscopic method for determining the components present in a sample, comprising:
illuminating the sample;
obtaining spectral data from a plurality of points on the sample;
making an initial estimate of spectral values of a first component of the sample;
from the estimate of the first component, performing an iterative resolution of the spectrum of the first component; and
making an initial estimate of spectral values of at least one further component of the sample, and performing an iterative resolution of the spectrum of each such component from the respective initial estimate and from one or more of the previously resolved spectra;

wherein equal values are used for all spectral values of a respective initial estimate.

3. A method according to claim 1, wherein respective initial estimates are made of spectral values of successive further components of the sample, and an iterative resolution of the spectrum of each such component is performed from the respective initial estimate and one or more previously resolved spectra.

4. A method according to claim 1, wherein the iterative resolutions use an alternating least squares technique.

5. A method according to claim 1, including storing the iteratively resolved spectral values of the components.

6. A method according to claim 1, wherein the spectral values are analysed to produce a map representing the concentrations of the components of the sample over an area thereof.

7. Apparatus for determining the components present in a sample, comprising a computer programmed to:
take spectral data obtained from a plurality of points on the sample;
make an initial estimate of spectral values of a first component of the sample;
from the estimate of the first component, perform an iterative resolution of the spectrum of the first component;
make an initial estimate of spectral values of at least one further component of the sample; and
perform an iterative resolution of the spectrum of each such component from the respective initial estimate and from one or more of the previously resolved spectra;
wherein equal values are used for all spectral values of a respective initial estimate.

8. Apparatus according to claim 7, further comprising a spectroscopic analysis device for obtaining the spectral data from the plurality of points on the sample.

9. A non-transitory computer readable medium storing a computer-executable program for determining the components present in a sample, the program comprising:
instructions for accessing spectral data obtained from a plurality of points on the sample;
instructions for making an initial estimate of spectral values of a first component of the sample;
instructions for performing, from the estimate of the first component, an iterative resolution of the spectrum of the first component;
instructions for making an initial estimate of spectral values of at least one further component of the sample; and
instructions for performing an iterative resolution of the spectrum of each such component from the respective initial estimate and from one or more of the previously resolved spectra;
wherein equal values are used for all spectral values of a respective initial estimate.

10. A method according to claim 2, wherein respective initial estimates are made of spectral values of successive further components of the sample, and an iterative resolution of the spectrum of each such component is performed from the respective initial estimate and one or more previously resolved spectra.

11. A method according to claim 2, wherein the iterative resolutions use an alternating least squares technique.

12. A method according to claim 2, including storing the iteratively resolved spectral values of the components.

13. A method according to claim 2, wherein the spectral values are analysed to produce a map representing the concentrations of the components of the sample over an area thereof.

14. Apparatus according to claim 7, wherein the computer is programmed to make respective initial estimates of spectral values of successive further components of the sample, and to perform an iterative resolution of the spectrum of each such component from the respective initial estimate and one or more previously resolved spectra.

15. Apparatus according to claim 7, wherein the iterative resolutions use an alternating least squares technique.

16. Apparatus according to claim 7, wherein the spectral values are analysed to produce a map representing the concentrations of the components of the sample over an area thereof.

* * * * *